United States Patent [19]

O'Lenick, Jr.

[11] Patent Number: 5,073,619

[45] Date of Patent: Dec. 17, 1991

[54] SILICONE AMPHOTERIC POLYMERS

[75] Inventor: Anthony J. O'Lenick, Jr., Lilburn, Ga.

[73] Assignee: Siltech Inc., Norcross, Ga.

[21] Appl. No.: 564,785

[22] Filed: Aug. 9, 1990

Related US. Application Data

[63] Continuation-in-part of Ser. No. 448,308, Dec. 11, 1989, Pat. No. 4,973,643.

[51] Int. Cl.$^5$ .............................................. C08G 77/04
[52] U.S. Cl. ...................................... 528/26; 528/28; 556/413
[58] Field of Search ...................... 528/26, 28; 556/413

[56] References Cited

U.S. PATENT DOCUMENTS 4,587,321  5/1986  Sebag et al. ............................ 528/28
4,654,161  3/1987  Kollmeier et al. ................... 556/413
4,918,210  4/1990  Fenton et al. ........................... 528/28

*Primary Examiner*—John C. Bleutge
*Assistant Examiner*—Karen A. Hellender

[57] ABSTRACT

The invention discloses novel organofunctional silicone polymers which have an amphoteric pendant functionality. Compounds of the invention by virtue of their amphoteric structure are good detergents and foaming agents and essentially non irritating to eyes and skin. The compounds of the invention are nonirritating, and non yellowing and provide detergency and foam to many formulated products, including cosmetic and personal care products.

The compounds of the present invention are prepared by introduction of a amphoteric group by reaction of acrylic acid or methyl acrylate with a primary alkoxylated amine containing the silicone polymer.

10 Claims, No Drawings

SILICONE AMPHOTERIC POLYMERS

RELATED APPLICATIONS

This application is a continuation in part of U.S. Ser. No. 448,308 filed Dec. 11, 1989, now U.S. Pat. No. 4,973,643.

FIELD OF INVENTION

The present invention relates to a series of novel amphoteric silicone polymers which are outstanding detergents and foaming agents. The compounds provide detergence and foaming properties while being essentially nonirritating to skin and eye. The compounds also exhibit an inverse cloud point, becoming insoluble at temperatures above their inverse cloud point.

DESCRIPTION OF THE ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In most instances, commercially available quatarnary ammonium compounds are the active ingredient in traditional hair, skin and laundry care markets, with little or no silicone added.

The low efficiency and low durability of polydimethyl siloxane is due to the fact that it is very water insoluble and deposits minimally on the surface of the fiber. Simply, the silicone oil delivery to the surface is by hydrophobic binding, not chemical bonding. If delivered to the surface, the polydimethylsiloxane is a very effective fiber lubricant, however, there are two drawbacks, first: the polydimethylsiloxane is not chemically bonded so the effect is very transient and disappears with one washing, and second: since there is no reaction of the polydimethylsiloxane to the surface an equilibrium between fiber absorbed polydimethylsiloxane and polydimethylsiloxane in the dispersion results in very inefficient percentage of silicone deposited. A large amount of the expensive silicone goes down the drain with the waste water.

Many attempts have been made to overcome these problems and get a truly substantive product, which deposits efficiently. One approach has been to use hydrosilation technology to make alkoxylated silicone polymers, used as raw materials in this invention. Hydrosilation technology is known to those skilled in the art and is outlined in U.S. Pat. No. 4,083,856. These materials, prepared by the hydrosilation of a vinyl alkoxylated alcohol and a silanic hydrogen containing polymer, by virtue of their alkoxylation, exhibit a high cloud point classically seen in nonionics, which is a point where at some elevated temperature, the silicone polymer comes out of solution and becomes more substantive to the hydrophobic substrate. This approach allows for better efficiencies but does little if anything for long term substantivity.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is an ether linkage and a new hydroxyl group. While a definite improvement over other compounds the efficiency and durability of these prior art compounds were not good enough to allow for cost effective incorporation of these materials in detergent formulations.

There has long been an interest in capitalizing on the low irritation properties of silicone polymers in personal care and other applications. One difficulty has been that many silicone compounds are insoluble in water and in fact defoam or inhibit the detergency activity in many systems.

OBJECT OF THE INVENTION

It is one of the objects of the present invention to provide novel amphoteric silicone polymers which are outstanding nonirritating detergents and foaming agents.

It is another objective of the current invention to provide amphoteric silicone polymers which can be used in personal care products.

Still another object of the present invention is to provide a series of products which have differing solubilities in water and organic solvents. This is achieved by selection of the hydroxyl silicone raw material.

THE INVENTION

Summary of the Invention

The present invention relates to novel amphoteric silicone polymers which have an amphoteric pendant functional group. The polymers by virtue of the amphoteric pendent group are excellent detergents and foaming agents.

More specifically, the compounds of the present invention are amphoterics of the propionate class. This class of materials are capable of existing in three distinct forms as a function of pH.

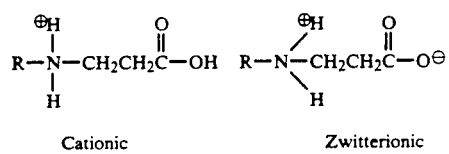

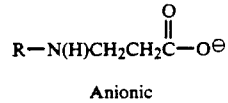

The propionates are further divided into the mono carboxylic form called the amino and the di carboxylic called the imino.

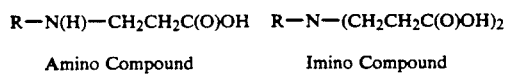

The propionates act primarily as cationic materials below the isoelectric range, amphoteric within it, and anionic above it.

The ampholytes are amphoterics having a quaternized nitrogen function and a carboxyllic function. The compounds are ampholytes since they exist in only two forms as a function of pH. This distinguishes them from amphoterics.

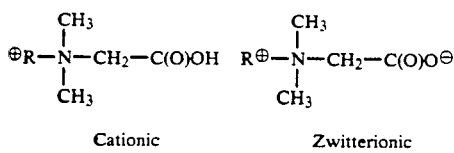

Cationic    Zwitterionic

The compounds of the present invention conform to the following structure;

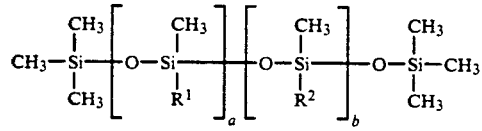

a is an integer from 1 to 200;
b is an integer from 1 to 200;
$R^1$ is selected from $-(CH_2)_nCH_3$ and phenyl;
n is an integer from 0 to 10;
$R^2$ is $-(CH_2)_3-(OCH_2CH_2)x-(OCH_2CH(CH_3))y-(OCH_2CH_2)z-R^3$;
x, y and z are integers and are independently selected from 0 to 20;

$R^3$ is

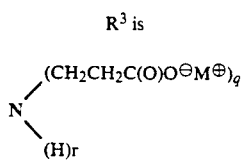

q ranges from 1 to 2;
r ranges from 0 to 1 with the proviso that q+r=2;
M is needed for charge balance and is selected from Na, K, Li, $NH_4$, or H.

The products of the present invention are prepared by reaction of an alkoxylated silicone amine polymer marketed by Siltech Inc. under the trade name SILUBE, and are described in copending U.S. patent application Ser. No. 448,308 filed 12/11/1989, with acrylic acid or methyl acrylate.

The compounds described in Ser. No. 448,308 have a pendant alkoxyamino group as represented by the following formula;

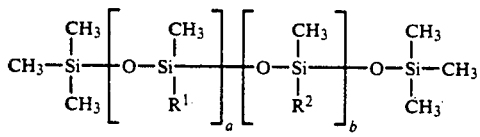

a is an integer from 1 to 200;
b is an integer from 1 to 200;
$R^1$ is selected from $-(CH_2)_nCH_3$ and phenyl;
n is an integer from 0 to 10;
$R^2$ is $-(CH_2)_3-(OCH_2CH_2)x-(OCH_2CH(CH_3))y-(OCH_2CH_2)z-R^3$;
x, y and z are independently integers selected from 0 to 20;
$R^3$ is $-NH_2$.

The amino compounds used as raw materials in the preparation of the compounds of the current invention, are described in copending U.S. patent application Ser. No. 448,308 are prepared by reaction of a hydroxyl containing silicone polymer with a suitable aminating reagent. These materials are marketed by Siltech Inc. Norcross, Ga. under the SILUBE Trade name.

| Reactant Class 1 | | Alkoxy Amino Silicone Reactants | | | | |
|---|---|---|---|---|---|---|
| Example | $R^1$ | a | b | x | y | z |
| 1 | Methyl | 100 | 2 | 0 | 0 | 0 |
| 2 | Methyl | 150 | 2 | 1 | 1 | 1 |
| 3 | Methyl | 50 | 2 | 10 | 10 | 10 |
| 4 | Methyl | 200 | 3 | 0 | 10 | 0 |
| 5 | Methyl | 25 | 1 | 20 | 20 | 20 |
| 6 | Methyl | 50 | 1 | 0 | 0 | 0 |
| 7 | Octyl | 170 | 2 | 5 | 0 | 0 |
| 8 | Phenyl | 180 | 2 | 0 | 0 | 0 |
| 9 | Phenyl | 150 | 3 | 3 | 0 | 0 |
| 10 | Phenyl | 50 | 2 | 5 | 1 | 5 |

Reactant Class 2

Suitable materials used as reactants for the current invention include acrylic acid, methyl acrylate, crotonic acid and methacrylic acid.

SILICONE AMPHOTERIC PREPARATION EXAMPLES

General Procedure

In a suitable three neck flask equipped with agitation and thermometer, is added 10,000 grams of water, 72.0 grams of acrylic acid and 500 ppm hydroquinone mono methylether. Next, the specified amount of the specified silicone amine reactant (examples 1-10 ) is added. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough base to neutralize the product to a pH of 7 to 8. Addition is exothermic and is controlled by submersion of the flask into a cooling bath.

| Example | Alkoxy Amino Silicone Example Number | Alkoxy Amino Silicone weight in grams |
|---|---|---|
| 11 | 1 | 3,737.0 |
| 12 | 2 | 5,588.0 |
| 13 | 3 | 1,898.0 |
| 14 | 4 | 4,965.0 |
| 15 | 5 | 1,984.0 |
| 16 | 6 | 3,795.0 |
| 17 | 7 | 6,400.0 |
| 18 | 8 | 6,730.0 |
| 19 | 9 | 3,745.0 |
| 20 | 10 | 1,921.0 |

The products of the above reaction are all mono-carboxylates (amino compounds).

$R^3$ is

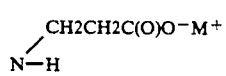

Diadducts

In a suitable three neck flask equipped with agitation and thermometer, is added 10,000 grams of water, 144.0 grams of acrylic acid and 500 ppm hydroquinone mono methylether. Next, the specified amount of the specified silicone amine reactant (examples 1-10) is added. The reaction mass will thicken as heat is applied. At about 80°-90° C. the viscosity thins out. Hold at this temperature 5 to 9 hours. The reaction is complete whin the tertiary amine concentration reaches at least 97% of theoretical.

Add enough base to neutralize the product to a pH of 7 to 8. Addition is exothermic and is controlled by submersion of the flask into a cooling bath.

| Example | Alkoxy Amino Silicone Example Number | Alkoxy Amino Silicone weight in grams |
|---------|--------------------------------------|---------------------------------------|
| 21 | 1 | 3,737.0 |
| 22 | 2 | 5,588.0 |
| 23 | 3 | 1,898.0 |
| 24 | 4 | 4,965.0 |
| 25 | 5 | 1,984.0 |
| 26 | 6 | 3,795.0 |
| 27 | 7 | 6,400.0 |
| 28 | 8 | 6,730.0 |
| 29 | 9 | 3,745.0 |
| 30 | 10 | 1,921.0 |

The products of the above reactions (Examples 21-30) are di-carboxylates (imino compounds).
$R^3$ is $-N-(CH_2CH_2C(O)O\ M^-)_2{}^+$ Applications Data

| Function | Amino | Imino |
|----------|-------|-------|
| Wetting | Fast | Slow |
| Water solubility | Decreased | Increased |
| Surface Activity | Increased | Decreased |
| Oil Solubility | Increased | Decreased |

Foam

The compounds of the invention were found to be excellent foamers, giving dense, copious foam.

Test Method

1% surfactant 50 ml shaken in a graduated cylinder

Results

| Example | Type | Foam Initial ml | Foam 5 Min ml |
|---------|------|-----------------|---------------|
| 29 | Amphoteric | 188 | 98 |
| 39 | Amphoteric | 150 | 87 |
| 41 | Amphoteric | 176 | 100 |

The compounds of the present invention can be included in several personal care products for low irritation detergency. One such example is as follows;

| HAND AND BODY LOTION | |
|---|---|
| Ingredients | % by weight |
| Mineral oil, light | 5.0 |
| PEG-5 soya sterol | 2.5 |
| Stearic acid | 3.0 |
| Cetyl alcohol | 2.8 |
| Isopropyl isostearate | 2.5 |
| Example 22 | 1.5 |
| Glycerin | 5.0 |
| Water | QS |

What is claimed:

1. A silicone amphoteric polymer which conforms to the following structure;

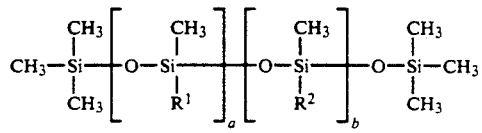

a is an integer from 1 to 200;
b is an integer from 1 to 200;
$R^1$ is selected from $-(CH_2)_nCH_3$ and phenyl;
n is an integer from 0 to 10;
$R^2$ is $-(CH_2)_3-(OCH_2CH_2)x-(OCH_2CH(CH_3-))y-(OCH_2CH_2)z-R^3$;
x, y and z are integers and are independently selected from 0 to 20;
$R^3$ is

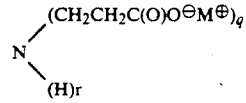

q is 1 or 2;
r is 0 or 1, with the proviso that $q+r=2$
M is needed for charge balance and is selected from Na, K, Li, NH$_4$, or H.

2. A compound of claim 1 wherein $R^1$ is CH$_3$.
3. A compound of claim 1 wherein $R^1$ is phenyl.
4. A compound of claim 1 wherein x is 3, y is 2 and z is 3.
5. A compound of claim 1 wherein x, y and z are independently selected from 5 to 10.
6. A compound of claim 1 wherein x, y and z are all 0.
7. A compound of claim 1 wherein q is 1.
8. A compound of claim 1 wherein q is 2.
9. A compound of claim 1 wherein M is H.
10. A compound of claim 1 wherein M is Na.

* * * * *